United States Patent
Harvey et al.

(10) Patent No.: US 6,331,533 B1
(45) Date of Patent: Dec. 18, 2001

(54) METHOD FOR INHIBITING DENTAL RESORPTIVE LESIONS

(75) Inventors: Colin E. Harvey, Ardmore, PA (US); Kenneth L. Mohn, Rahway, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/436,585

(22) Filed: Nov. 9, 1999

Related U.S. Application Data

(60) Provisional application No. 60/108,576, filed on Nov. 16, 1998.

(51) Int. Cl.$^7$ ............................................. A61K 31/66
(52) U.S. Cl. ................................. 514/108; 424/49; 424/57
(58) Field of Search ........................ 424/49–88; 514/108

(56) References Cited

U.S. PATENT DOCUMENTS

| | | | |
|---|---|---|---|
| 4,621,077 | 11/1986 | Rosini et al. | 514/108 |
| 4,705,651 | 11/1987 | Staibano | 260/502.5 |
| 4,922,007 | 5/1990 | Kieczykowski et al. | 562/13 |
| 5,019,651 | 5/1991 | Kieczykowski | 562/13 |
| 5,159,108 | 10/1992 | Kieczykowski | 562/13 |
| 5,270,365 | 12/1993 | Gertz et al. | 514/108 |
| 5,358,941 | 10/1994 | Bechard et al. | 514/102 |
| 5,409,911 | 4/1995 | Tyler et al. | 514/91 |
| 5,449,819 | 9/1995 | Venkataramani et al. | 562/13 |
| 5,462,932 | 10/1995 | Brenner et al. | 514/108 |
| 5,510,517 | 4/1996 | Dauer et al. | 562/13 |
| 5,589,691 | 12/1996 | Venkataramani et al. | 252/182.11 |
| 5,616,571 | 4/1997 | Daifotis et al. | 514/102 |
| 5,646,134 | 7/1997 | Yates | 514/108 |
| 5,648,491 | 7/1997 | Dauer et al. | 546/22 |
| 5,652,227 | 7/1997 | Teronen et al. | . |
| 5,658,756 | 8/1997 | Rodan et al. | 435/69.1 |
| 5,663,195 | 9/1997 | Scolnick | 514/461 |
| 5,681,590 | 10/1997 | Bechard et al. | 424/464 |
| 5,733,564 | 3/1998 | Lehtinen | . |
| 5,780,455 | 7/1998 | Brenner et al. | 514/108 |
| 5,804,570 | 9/1998 | Santora, II et al. | 415/108 |
| 5,843,924 | 12/1998 | Brenner et al. | 514/108 |
| 5,849,726 | 12/1998 | Brenner et al. | 514/108 |
| 5,853,759 | 12/1998 | Katdare et al. | 424/466 |
| 5,882,656 | 3/1999 | Bechard et al. | 424/400 |
| 5,891,863 | 4/1999 | Yates | 514/108 |
| 5,914,099 | 6/1999 | Yates et al. | 424/49 |
| 5,914,323 | 6/1999 | Brenner et al. | 514/108 |
| 5,958,908 | 9/1999 | Dohi et al. | 514/108 |
| 5,972,913 | 10/1999 | Yates | 514/108 |
| 5,994,329 | 11/1999 | Daifotis et al. | 514/108 |
| 5,998,390 | 12/1999 | Ramamurthy et al. | . |
| 6,008,206 | 12/1999 | Dohi et al. | 514/108 |
| 6,008,207 | 12/1999 | Brenner et al. | 514/108 |
| 6,015,801 | 1/2000 | Daifotis et al. | . |

OTHER PUBLICATIONS

Jowsey et al J: Lab. Clin. Med. 76(1):126–133 Effect of Sodium Etidronate in Adult Cats, 1970.*

Gotcher et al J. Periodont. Res. 16(4):441–455 The Effects of a Diphosphonate on the Periodontium of the Rice Cat, 1981.*

Jowsey et al J. Lab. Clin. Med. 82(4): 567–575 Influence of Diphosphonates on Progress of Experimentally Induced Osteoporosis in Cats, 1973.*

Ellsasser et al Clin. Orthop. Relat. Res. 91:235–242 Effect of Low Doses of Disodium Ethane–1–Hydroxy–1, 1–Diphosphonate on Disuse Osteoporosis in Denervated amd Control Cats, 1973.*

Lund et al JAVMA 212 (3): 392–395 Prevalence, Risk Factors Odontoclastic Resorptive Lesions in Cats, Feb. 1998.*

Van Wessum et al Vet. Clin. No. Amer. Small Anim. 22(6):1405–1416 Feline Dental Resorptive Lesions. Prevalence Patterns, Nov. 1992*

Abstracts of Diphosphonates for Lesions.*

Buskes et al Caries Res. 19(6): 490–496 Lesion Formation and Lesion Remineralisation, 1985.*

Ten Cate Dutch Article The Role of Fluorides and Diphosphonates in the Formation of Sub Surface Carious Lesions, 1983.*

Mor et al N.Z. Dent JL. (348):57–61 Artifical Caries–Like Lesions—Diphosphonates, 1981.*

Ten Cate et al. Caries Res. 15(1): 60–69 Influence of Diphosphonates on Remineralisation of Artifical Enamel Lesions, 1981.*

Featherstone Arch Oral Biol. 23(5): 397–404 Diphosphonates Early Caries–Like Lesions of Human Tooth Enamel, 1978.*

Featherstone J. Dent. Res. 56 Spec D D48–D52 Diphosphonat (MHDP) Produced Artificial Carious Lesions, 1977.*

Riviere et al., Infection and Immunity, vol. 59, No. 10 (1991), pp. 3377–3380, "Pathogen–related oral spirochetes from dental plaque are invasive".

(List continued on next page.)

*Primary Examiner*—Shep K. Rose
(74) *Attorney, Agent, or Firm*—Anthony D. Sabatelli; Melvin Winokur; Nicole M. Wallinger

(57) ABSTRACT

The present invention relates to a method for inhibiting dental resorptive lesions and other disease states associated with dental resorptive lesions in a mammal by administering a therapeutically effective amount of a bisphosphonate or a pharmaceutically acceptable salt thereof to a mammal in need thereof. This invention also relates methods of alleviating of pain and reducing the risk of tooth loss associated with dental resorptive lesions in mammals.

20 Claims, 1 Drawing Sheet

OTHER PUBLICATIONS

Lund et al., JAVMA, vol. 212, No. 3 (1998), pp. 392–395, "Prevalance and risk factors for odontoclastic resorptive lesions in cats".

van Wessum et al., Veterinary Clinics in North America: Small Animal Practice—Feline Dentistry, vol. 22, No. 6 (1992), pp. 1405–1416, "Feline dental resorptive lesions".

Reddy et al., J. Periodont., vol. 66 (1995), pp. 211–217, "Alendronate treatment of naturally–occurring periodontitis in beagle dogs".

Weinreb er al., J. Periodont. Res., vol. 29 (1994), pp. 35–40, "Histomorphometrical analysis of the effects of the bisphosphonate alendronate on bone less caused by experimental periodontitis in monkeys".

Okuda et al., The Compendium (on continuing education for the practicing veterinarian), vol. 17, No. 12, (1995), pp. 1461–1469: "Challenges in treatment of external odontoclastic resorptive lesions in cats".

* cited by examiner

METHOD FOR INHIBITING DENTAL RESORPTIVE LESIONS

This application claims benefit of Prov. No. 60/108,576 filed Nov. 16, 1998.

FIELD OF THE INVENTION

The present invention relates to a method for inhibiting dental resorptive lesions and other disease states associated with dental resorptive lesions.

BACKGROUND OF THE INVENTION

Dental resorptive lesions have become one of the most common dental diseases in cats and are occurring with increasing frequency in other species, including humans. Dental resorptive lesions are also known by a variety of other names including odontoclastic resorptive lesions, feline neck lesions, cervical line lesions, chronic subgingival tooth erosions, feline external resorptive lesions, and/or subgingival resorptive lesions. This disease is characterized by cavitating lesions produced by osteoclastic (odontoclastic) resorption originating subgingivally and progressively eroding through the enamel/cementum and dentin layers into the pulpal tissues of the tooth. Odontoclasts are large multinucleated cells of up to about 400 nm in diameter and appear to be derived from the same lineage as osteoclasts, which are the cells responsible for bone resorption. The odontoclasts progressively attack apparently healthy tooth substance, producing large painful tooth lesions, ultimately resulting in tooth breakage with retention of root fragments in the gum.

Observation of dental resorptive lesions during routine examination of cats can be difficult because relatively little erosion of the cementum and enamel may be evident at the buccal surface. However, the lesion is apparent when examined radiographically. Although the lesion may not be obvious, it is commonly accompanied by signs of pain. Other clinical' signs include anorexia, concurrent gingivitis, and excessive salivation. See Elizabeth M. Lund, et al., *Prevalence and risk factors for odontoclastic resorptive lesions in cats, JAVMA*, Vol. 212, No. 3, pp. 392–95 (Feb. 1, 1998), which is incorporated by reference herein in its entirety.

The primary cause of dental resorptive lesions is not definitively known. Possible causes include oral inflammation, plaque or periodontal disease, systemic disease conditions, dietary factors, breed predisposition, and defects and diseases in the tissues of the tooth or periodontium. Of the studies done on feline dental resorptive lesions, the prevalence of the lesions consistently increases with age. See van Wessum, et al., *Feline Dental Resorptive Lesions, Veterinary Clinics of North America. Small Animal Practice*, Vol. 22, No. 6, pp. 1405–16 (November 1992), which is incorporated by reference herein in its entirety.

Dental resorptive lesions are distinguishable from other dental diseases, such as periodontal disease, dental caries and alveolar bone loss. Periodontal disease and dental caries are caused by aggressive bacterial or microbial build Up due to poor oral hygiene, malocclusion, tartar build up, food impaction and faulty dental restorations. See Riviere et al., *Infection and Immunity*, 59(10), 3377–80 (1991), Reddy et al., *J Periodontol*, 211–217 (March 1995), and Weinreb et al., *J. Periodont Res*, 29, 35–40 (1994), which are all incorporated by reference herein in their entirety. In periodontal disease, inflammation of the gum around the tooth results in leaching of the alveolar bone causing the teeth to become loose and to eventually fall out. In contrast, dental resorptive lesions can occur in the absence of periodontal disease and are caused by odontoclastic attack on the tooth surface itself, as opposed to the surrounding bone.

Currently, there is no effective treatment for dental resorptive lesions. Often, the affected teeth break off, thus creating the potential for root sequestrum formation and subsequent infection. Typically, affected teeth must be extracted because attempts to save the tooth by drilling out the lesion and filling it with restorative materials are ineffective. Approximately 90% of the repair attempts fall out within two years because of ongoing resorption. In addition, new lesions often develop in other teeth within the mouth of an affected individual. See Ayako Okuda, et al., *Challenges in Treatment of External Odontoclastic Resorptive Lesions in Cats, Compendium on Continuing Education for the Practicing Veterinarian*, Vol. 17, No. 12, pp. 1461–69 (December 1995), which is incorporated by reference herein in its entirety.

Even though dental resorptive lesions are currently observed primarily in cats, there is the potential for the spread of this disease to other mammalian species, including man. For example, before the 1950s, the presence of feline dental resorptive lesions was extremely rare. However, recent studies have calculated prevalence rates of 28.5% to 57% in the last ten years. See van Wessum, et al., *Feline Dental Resorptive Lesions, Veterinary Clinics of North America: Small Animal Practice*, Vol. 22, No. 6, pp. 1405 (November 1992). Therefore, there is a need to treat and/or reduce the risk of the condition and its spread.

Bisphosphonates are known in the art to bond to hydroxyapatite in bone and to inhibit the bone resorptive activity of osteoclasts. See H. Fleisch, *Bisphosphonates In Bone Disease, From The Laboratory To The Patient*, 3rd Edition, Parthenon Publishing (1997), which is incorporated by reference herein in its entirety. For example, bisphosphonates are known to be useful in the treatment of such diseases as osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation. Even though bisphosphonates have been used to treat the above-mentioned diseases, they have not been used to treat dental resorptive lesions.

It is surprisingly been found in the present invention that bisphosphonates are effective for inhibiting, i.e. treating and reducing the risk of contracting, dental resorptive lesions. Without being limited by theory, it is believed that new tooth substance is formed by odontoblasts to heal the lesions. Thus, administration of a bisphosphonate can eliminate the need for tooth extraction and its associated complications.

It is also surprisingly found in the present invention that a therapeutically effective amount of a bisphosphonate can be selectively delivered to the subgingival tooth surface and alveoli dentales such that at about 24 hours after administration the resulting average concentration of the bisphosphonate at the subgingival tooth surface and alveoli dentales is at least about two times greater than the average concentration in the skeleton, for example at the diaphysis of the femur.

Because it is estimated that greater than about 25% of cats visiting a veterinarian for any reason have dental resorptive lesions, what is desired in the art is a therapy to optimally inhibit the progression of clinically detectable, active dental resorptive lesions and to reduce the risk of the development of new lesions within the mouth of the affected individual. Also desired is a therapy to eliminate the need for tooth extraction and to alleviate the pain associated with dental resorptive lesions. It is desired that these therapeutics be used to both control the disease in cats and to reduce the risk of the spread of dental resorptive lesions to other species, including humans.

It is an object of the present invention to provide a method for inhibiting dental resorptive lesions in a mammal by administering a bisphosphonate or a pharmaceutically acceptable salt thereof.

It is another object of the present invention to provide a method for treating or reducing the risk of contracting dental resorptive lesions in a mammal by administering a bisphosphonate or a pharmaceutically acceptable salt thereof.

It is another object of the present invention to provide a method for inhibiting dental resorptive lesions in a cat by administering a bisphosphonate or a pharmaceutically acceptable salt thereof.

It is another object of the present invention to provide a method of alleviating the pain associated with dental resorptive lesions in a mammal by administering a bisphosphonate or a pharmaceutically acceptable salt thereof.

It is another object of the present invention to provide a method of reducing the risk of tooth loss associated with dental resorptive lesions in a mammal by administering a bisphosphonate or a pharmaceutically acceptable salt thereof.

It is another object of the present invention to selectively deliver a therapeutically effective amount of a bisphosphonate or a pharmaceutically acceptable salt thereof to the subgingival tooth surface and alveoli dentales.

These and other objects will become readily apparent from the detailed description which follows.

SUMMARY OF THE INVENTION

The present invention relates to a method for inhibiting dental resorptive lesions and other disease states associated with dental resorptive lesions.

In one embodiment, the present invention relates to a method for inhibiting, that is treating or reducing the risk of contracting, dental resorptive lesions in a mammal in need thereof comprising administering to said mammal a therapeutically effective amount of a bisphosphonate or a pharmaceutically acceptable salt thereof.

In a class of the embodiment, the mammal is a cat, preferably over two years old.

In a second class of the embodiment the bisphosphonate is selected from the group consisting of alendronate, cimadronate, clodronate, tiludronate, etidronate, ibandronate, neridronate, olpandronate, risedronate, piridronate, pamidronate, zoledronate, pharmaceutically acceptable salts thereof, and mixtures thereof; preferably the bisphosphonate is alendronate, and pharmaceutically acceptable salts thereof, more preferably, alendronate monosodium trihydrate.

In a second embodiment, the present invention relates to a method for alleviating the pain associated with dental resorptive lesions in a mammal in need thereof comprising administering to said mammal a pharmaceutically effective amount of a bisphosphonate or a pharmaceutically acceptable salt thereof.

In a class of the second embodiment, the mammal is a cat, preferably over two years old.

In a second class of the second embodiment, the bisphosphonate is selected from the group consisting of alendronate, cimadronate, clodronate, tiludronate, etidronate, ibandronate, neridronate, olpandronate, risedronate, piridronate, pamidronate, zoledronate, pharmaceutically acceptable salts thereof, and mixtures thereof, preferably the bisphosphonate is alendronate, more preferably, alendronate monosodium trihydrate.

In a third embodiment, the present invention relates to a method for reducing the risk of tooth loss associated with dental resorptive lesions in a mammal in need thereof comprising administering to said mammal a pharmaceutically effective amount of a bisphosphonate or a pharmaceutically acceptable salt thereof.

In a class of the third embodiment, the mammal is a cat, preferably over two years old.

In a second class of the third embodiment, the bisphosphonate is selected from the group consisting of alendronate, cimadronate, clodronate, tiludronate, etidronate, ibandronate, neridronate, olpandronate, risedronate, piridronate, pamidronate, zoledronate, pharmaceutically acceptable salts thereof, and mixtures thereof, preferably the bisphosphonate is alendronate, more preferably, alendronate monosodium trihydrate.

In a fourth embodiment, the present invention relates to the use of a bisphosphonate or a pharmaceutically acceptable salt thereof in the manufacture of a medicament for inhibiting dental resorptive lesions in a mammal in need thereof.

In a fifth embodiment, the present invention relates to a method for delivering a bisphosphonate or a pharmaceutically acceptable salt thereof to the subgingival tooth surface and alveoli dentales of a mammal comprising administering a therapeutically effective amount of said bisphosphonate to a mammal in need thereof such that at about 24 hours after administration the resulting average concentration of said bisphosphonate at said subgingival tooth surface and alveoli dentales is at least about two times greater than the average concentration in the diaphysis of the femur.

All percentages and ratios used herein, unless otherwise indicated, are by weight. The invention hereof can comprise, consist of, or consist essentially of the essential as well as optional ingredients, components, and methods described herein.

DETAILED DESCRIPTION OF THE INVENTION

Figure 1:
FIG. 1 shows an autoradiograph of a 30 micron thick section of feline maxilla 24 hours after treatment with a single 0.03 mg/kg dose of $^{14}C$ labelled alendronate monosodium trihydrate, wherein the $^{14}C$ label is at the 4-carbon position of the butyl group.

The present invention relates to a method for inhibiting dental resorptive lesions in a mammal in need thereof. In addition, the present invention relates to a method for alleviating the pain or reducing the risk of tooth loss associated with dental resorptive lesions in a mammal. The methods of the present invention comprise administering to the mammal a therapeutically effective amount of a bisphosphonate, or a pharmaceutically effective amount thereof. Representative mammals include humans, other primates, ruminants, etc. The present invention is particularly useful for inhibiting dental resorptive lesions in cats, especially in cats that are at least two years old. By inhibiting the formation of dental resorptive lesions, the bone loss that is associated with the disease can also be treated and/or the risk of such bone loss can be reduced. The administration of a bisphosphonate can alter odontoclast formation or activity, and thus successfully inhibit bone loss.

The term "inhibiting", as used herein, is intended to include both treating and reducing the risk of contracting, i.e. preventing, dental resorptive lesions.

The term "therapeutically effective amount", as used herein, means that amount of the bisphosphonate compound, that will elicit the desired therapeutic effect or response when administered in accordance with the desired treatment regimen. A preferred therapeutically effective amount of the bisphosphonate is a dental resorptive lesion inhibiting amount.

The term "pharmaceutically acceptable" as used herein means that the salts and derivatives of the bisphosphonates have the same general pharmacological properties as the free acid form from which they are derived and are acceptable from a toxicity viewpoint.

The term pharmaceutically acceptable salt, as used herein refers to non-toxic salts of the compounds useful in the instant invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Pharmaceutically acceptable salts also specifically include hydrates as well as the anhydrous forms.

The dosage regimen utilizing the compounds of the present invention is selected in accordance with a variety of factors including type, species, age, weight, sex and medical condition of the patient or subject; the severity of the condition to be treated; the route of administration; the renal and hepatic function of the patient or subject; and the particular compound or salt thereof employed. An ordinarily skilled physician, veterinarian or clinician can readily determine and prescribe the effective amount of the drug required to treat or reduce the risk of contracting the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.01 to 5.0 mg/kg/day. As a treatment, alendronate would be administered to mammals with clinically detectable resorptive lesions at an adequate dose to arrest odontoclastic destruction, preferably 0.01 to 0.1 mg/kg intravenously or subcutaneously, or 1.0 to 5.0 mg/kg orally. As a preventative, alendronate would be administered at a dose which blocks odontoclastic attack, preferably 0.01 to 0.05 mg/kg intravenously or subcutaneously, or 1.0 to 3.0 mg/kg orally at an appropriate rate to reduce the risk of occurrence of resorptive lesions. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Advantageously, compounds of the present invention can be administered in a single daily dose, a total daily dosage administered in divided doses of two, three or four times daily, a weekly dose, a biweekly dose, a monthly dose, or a dose administered every 3 to 6 months. Furthermore, compounds of the present invention can be administered in intranasal form via use of suitable intranasal vehicles, or via transdermal routes, using those forms of transdermal delivery systems well known to those of ordinary skill in the art. To be administered in the form of a transdermal delivery system, the dosage administration can be an immediate single unit dose or can be sustained release systems using either continuous or intermittent delivery.

For methods of treatment of the present invention, the bisphosphonate compound is continuously administered until the desired change in tooth structure is observed. In such instances, the inhibition of the progression of clinically detectable, active dental resorptive lesions and the relief of pain associated with such lesions are the desired objectives. For methods of prevention of the present invention, the bisphosphonate compound is continuously administered for as long as necessary to reduce the risk of contracting the onset of dental resorptive lesions. Nonlimiting examples of administration periods can range from about 2 weeks to the remaining lifespan of the mammal. For cats, administration periods can range from about 2 weeks to the remaining life span of the cat, which is up to about 20 years. For humans, administration periods can range from about 2 weeks to the remaining lifespan of the human. Nonlimiting examples of administration to humans can range from about 2 weeks to about 20 years, from about 1 month to about 20 years, from about 6 months to about 10 years, and from about 1 year to about 10 years.

Methods of Selectively Delivering Bisphosphonates

The present invention also relates to methods for selectively delivering a bisphosphonate or a pharmaceutically acceptable salt thereof to the target areas of the oral tissues wherein it is desired to treat and/or reduce the risk of contracting dental resorptive lesions.

In the present invention, a therapeutically effective amount of a bisphosphonate or pharmaceutically acceptable salt thereof is selectively delivered to the subgingival tooth surface and alveoli dentales, i.e. the tooth sockets, of a mammal. The selectivity is such that at about 24 hours after administration of the bisphosphonate, the resulting average concentration of the bisphosphonate at the subgingival tooth surface and alveoli dentales is at least about two times greater than the average concentration in the diaphysis, i.e. the midshaft section, of the femur. The amount of bisphosphonate present can be quantitated by treating an animal with an appropriately radiolabelled bisphosphonate and analyzing the amount of radiolabelled material present in a bone biopsy from a donor subject or in a larger sample taken from a sacrificed animal. Also, the amount can be quantitated using an appropriately radiolabelled bisphosphonate (e.g., $^{14}C$ labelled alendronate monosodium trihydrate) in conjunction with autoradiography and densitometry measurements.

Bisphosphonates

The methods and compositions of the present invention comprise the adminstration of a bisphosphonate or a pharmaceutically acceptable salt thereof. The bisphosphonates of the present invention correspond to the chemical formula

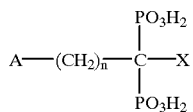

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring.

In the foregoing chemical formula, the alkyl groups can be straight, branched, or cyclic, provided sufficient atoms are selected for the chemical formula. The C1–C30 substituted alkyl can include a wide variety of substituents, nonlimiting examples which include those selected from the group consisting of phenyl, pyridyl, furanyl, pyrrolidinyl, imidazonyl, $NH_2$, C1–C10 alkyl or dialkyl substituted $NH_2$, OH, SH, and C1–C10 alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

A non-limiting class of structures useful in the instant invention are those in which A is selected from the group consisting of H, OH, and halogen, and X is selected from the group consisting of C1–C30 alkyl, C1–C30 substituted alkyl, halogen, and C1–C10 alkyl or phenyl substituted thio.

A non-limiting subclass of structures useful in the instant invention are those in which A is selected from the group consisting of H, OH, and Cl, and X is selected from the group consisting of C1–C30 alkyl, C1–C30 substituted alkyl, Cl, and chlorophenylthio.

A non-limiting example of the subclass of structures useful in the instant invention is when A is OH, X is a 3-aminopropyl moiety and n is zero, so that the resulting compound is a 4-amino-1,-hydroxybutylidene-1,1-bisphosphonate, i.e. alendronate.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1–C30-alkyl-substituted ammonium. Preferred salts are those selected from the group consisting of sodium, potassium, calcium, magnesium, and ammonium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid). 1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

A non-limiting class of bisphosphonates useful in the instant invention are selected from the group consisting of alendronate, cimadronate, clodronate, tiludronate, etidronate, ibandronate, risedronate, piridronate, pamidronate, zoledronate, pharmaceutically acceptable salts thereof, and mixtures thereof.

A non-limiting subclass of the above-mentioned class useful in the instant case contains alendronate, pharmaceutically acceptable salts thereof, and mixtures thereof.

A non-limiting example of the subclass is alendronate monosodium trihydrate.

Pharmaceutical Compositions

The compounds of the present invention can be administered in such oral dosage forms as tablets, capsules (each of which includes sustained release or timed release formnulations), pills, powders, granules, elixers, tinctures, suspensions, syrups, pastes, gels, solutions, and emulsions. Likewise, they may also be administered in intravenous (bolus or infusion), intraperitoneal, nasal sprays, suppositories, tooth pastes (i.e. dentrifices which are also useful for cleansing the teeth), topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as a treatment for dental resorptive lesions.

Compositions useful in the present invention comprise a pharmaceutically effective amount of a bisphosphonate or a pharmaceutically acceptable salt thereof. The bisphosphonate is typically administered in admixture with suitable pharmaceutical diluents, excipients, or carriers, collectively referred to herein as "carrier materials", suitably selected with respect to oral administration, i.e. tablets, capsules, elixirs, syrups, effervescent compositions, powders, and the like, and consistent with conventional pharmaceutical practices. For example, for oral administration in the form of a tablet, capsule, or powder, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like; for oral administration in liquid form, e.g., elixirs and syrups, effervescent compositions, the oral drug components can be combined with any oral, non-toxic, pharmaceutically acceptable inert carrier such as ethanol, glycerol, water and the like. Moreover, when desired or necessary, suitable binders, lubricants, disintegrating agents, buffers, coatings, and coloring agents can also be incorporated. Suitable binders can include starch. gelatin, natural sugars such as glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. A tablet formulations for alendronate monosodium trihydrate and other bisphosphonates are described in U.S. Pat. No. 5,358,941, to Bechard et al, issued Oct. 25, 1994, and U.S. Pat. No. 5,681,590, to Bechard et al., issued October 28, 1997, which are both incorporated by reference herein in its entirety. Oral liquid alendronate formulations are described in U.S. Pat. No. 5,462,932, to Brenner et al, issued Oct. 31, 1995, which is incorporated by reference herein in its entirety. Intravenous alendronate formulations are described in U.S. Pat. No. 5,780,455, to Brenner et al, issued Jul. 14, 1998, which is incorporated by reference herein in its entirety. The compounds used in the present method can also be coupled with soluble polymers as targetable drug carriers. Such polymers can include polyvinylpyrrolidone, pyran copolymer, polyhydroxylpropyl-methacrylamide, and the like.

The precise dosage of the bisphonate will vary with the dosing schedule, the oral potency of the particular bisphosphonate chosen, the age, size, sex and condition of the recipient subject, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a dental resorptive lesion inhibiting effect, i.e. a dental resorptive lesion inhibiting amount.

EXAMPLES

The following examples further describe and demonstrate embodiments within the scope of the present invention. The examples are given solely for the purpose of illustration and are not to be construed as limitations of the present invention as many variations thereof are possible without departing from the spirit and scope of the invention.

EXAMPLES OF PHARMACEUTICAL COMPOSITIONS

Pharmaceutical Tablet Compositions

Tablets are prepared using standard mixing and formation techniques as described in U.S. Pat. No. 5,358,941, to Bechard et al., issued Oct. 25, 1994, which is incorporated by reference herein in its entirety.

Tablets containing about 10 mg of alendronate monosodium trihydrate, on an alendronic acid active basis are prepared using the following relative weights of ingredients.

| Ingredient | Per Tablets | Per 4000 Tablets |
| --- | --- | --- |
| Alendronate Monosodium Trihydrate | 13.051 mg | 52.20 g |
| Anhydrous Lactose, NF | 71.32 mg | 285.28 g |
| Microcrystalline Cellulose, NF | 80.0 mg | 320.0 g |
| Magnesium Stearate, NF | 1.0 mg | 4.0 g |
| Croscarmellose Sodium, NF | 2.0 mg | 8.0 g |

The resulting tablets are useful for administration in accordance with the methods of the present invention for inhibiting, i.e. treating or reducing the risk of contracting, dental resorptive lesions in a mammal in need thereof.

Similarly, tablets comprising other relative weights of alendronate, on an alendronic acid active weight basis are prepared. Also, tablets containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, tablets containing combinations of bisphosphonates are similarly prepared.

Suspensions

| Ingredient | Percent W/W |
| --- | --- |
| Alendronate Monosodium Trihydrate | 1.3% w/w |
| Colloidal Silicon dioxide | 3.0 |
| Alpha-tocopherol | 0.2 |
| Fish Oil | 95.5 |

The resulting suspensions are useful for administration in accordance with the methods of the present invention for inhibiting, i.e. treating or reducing the risk of, dental resorptive lesions in a mammal in need thereof.

Similarly, suspensions comprising other relative weights of alendronate, on an alendronic acid active weight basis are prepared.

Also, suspensions containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, suspensions containing combinations of bisphosphonates are similarly prepared.

Solutions

| Ingredient | Percent W/V |
| --- | --- |
| A. | |
| Alendronate Monosodium Trihydrate | 1.3% w/v |
| Citric Acid | 1.0 |
| Sodium Citrate | 0.5 |
| Butterscotch Flavor | 0.2 |
| Purified Water | 97.0 |
| B. | |
| Alendronate Monosodium Trihydrate | 0.4% w/v |
| Sodium Carbonate | 0.7 |
| Sodium Bicarbonate | 0.6 |
| Tuna Water | 90.0 |
| Purified Water | 8.3 |

The resulting solutions are useful for administration in accordance with the methods of the present invention for inhibiting, i.e. treating or reducing the risk of, dental resorptive lesions in a mammal in need thereof.

Similarly, solutions comprising other relative weights of alendronate, on an alendronic acid active weight basis are prepared. Also, solutions containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, solutions containing combinations of bisphosphonates are similarly prepared.

Ointments

| Ingredient | Percent W/W |
| --- | --- |
| Alendronate Monosodium Trihydrate | 1.3% w/w |
| Lecithin | 3.0 |
| Malt Syrup | 45.0 |
| White Petrolatum | 50.7 |

The resulting ointments are useful for administration in accordance with the methods of the present invention for inhibiting, i.e. treating or reducing the risk of, dental resorptive lesions in a mammal in need thereof.

Similarly, ointments comprising other relative weights of alendronate, on an alendronic acid active weight basis are prepared. Also, ointments containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, ointments containing combinations of bisphosphonates are similarly prepared.

Gels

| Ingredient | Percent W/W |
| --- | --- |
| Alendronate Monosodium Trihydrate | 1.3% w/w |
| Citric Acid | 1.0 |
| Sodium Citrate | 0.5 |
| Poloxamer | 20.0 |
| Propylene Glycol | 20.0 |
| Benzyl Alcohol | 2.0 |
| Purified Water | 57.0 |

The resulting gels are useful for administration in accordance with the methods of the present invention for inhibiting, i.e. treating or reducing the risk of, dental resorptive lesions in a mammal in need thereof.

Similarly, gels comprising other relative weights of alendronate, on an alendronic acid active weight basis are prepared. Also, gels containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, gels containing combinations of bisphosphonates are similarly prepared.

Pastes

| Ingredient | Percent W/W |
| --- | --- |
| Alendronate Monosodium Trihydrate | 1.3% w/w |
| Sodium Carboxymethylcellulose | 2.0 |
| Magnesium aluminum Silicate | 2.0 |
| Methyl paraben | 0.18 |
| Propyl Paraben | 0.02 |
| Sorbitol Solution | 20.0 |
| Propylene Glycol | 20.0 |
| Purified Water | 54.5 |

The resulting pastes are useful for administration in accordance with the methods of the present invention (e.g., as a dentifrice) for inhibiting, i.e. treating or reducing the risk of, dental resorptive lesions in a mammal in need thereof.

Similarly, pastes comprising other relative weights of alendronate, on an alendronic acid active weight basis are prepared. Also, pastes containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, pastes containing combinations of bisphosphonates are similarly prepared.

Composition For Transdermal Delivery

| Ingredient | Percent W/V |
| --- | --- |
| Alendronate Monosodium Trihydrate | 1.3% w/v |
| Butylated Hydroxyanisole | 0.02 |
| Polysorbate 80 | 3.0 |
| Diethyleneglycol monobutyl ether | 5.0 |
| n-Methylpyrrolidone | 90.7 |

The resulting composition is useful for administration in accordance with the methods of the present invention for inhibiting, i.e. treating or reducing the risk of, dental resorptive lesions in a mammal in need thereof.

Similarly, a composition comprising other relative weights of alendronate, on an alendronic acid active weight basis are prepared. Also, compositions containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, compositions containing combinations of bisphosphonates are similarly prepared.

Composition For Transdermal Delivery (Skin Patch)

| Ingredient | Percent W/W |
| --- | --- |
| Alendronate Base | 5.0% w/w |
| Alcohol | 15.0 |
| Hydoxypropylcellulose | 1.0 |
| Mineral oil | 0.2 |
| Polyisobutylene | QSAD |
| Ethylenevinyl acetate | QSAD |

The resulting composition is useful for administration in accordance with the methods of the present invention for inhibiting, i.e. treating or reducing the risk of, dental resorptive lesions in a mammal in need thereof.

Similarly, compositions comprising other relative weights of alendronate, on an alendronic acid active weight basis are prepared.

Also, compositions containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, compositions containing combinations of bisphosphonates are similarly prepared.

Injectables (IV/IM,SC/IP)

| Ingredient | Percent W/V |
| --- | --- |
| Alendronate Monosodium Trihydrate | 2.0% w/V |
| Sodium Citrate | 0.5 |
| Benzyl Alcohol | 2.0 |
| Edetate Sodium | 0.01 |
| Sodium Metabisulfite | 0.02 |
| Water for Injection | 95.5 |

The resulting injectables are useful for administration in accordance with the methods of the present invention for inhibiting, i.e. treating or reducing the risk of, dental resorptive lesions in a mammal in need thereof.

Similarly, injectables comprising other relative weights of alendronate, on an alendronic acid active weight basis are prepared. Also, injectables containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, injectables containing combinations of bisphosphonates are similarly prepared.

Compositions for Intra-Nasal Delivery

| Ingredient | Percent W/W |
| --- | --- |
| Alendronate Monosodium Trihydrate | 2.0% w/w |
| Carboxymethylcellulose sodium | 0.2 |
| Dextrose | 0.9 |
| Benzylalkonium chloride | 0.01 |
| Polysorbate 80 | 3.0 |
| Hydrochloric acid | 0.01 |
| Purified Water | 93.9 |

The resulting composition is useful for administration in accordance with the methods of the present invention for inhibiting, i.e. treating or reducing the risk of, dental resorptive lesions in a mammal in need thereof.

Similarly, compositions comprising other relative weights of alendronate, on an alendronic acid active weight basis are prepared. Also, compositions containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, compositions containing combinations of bisphosphonates are similarly prepared.

Sustained-Release Tablets

| Ingredient | Percent W/W |
| --- | --- |
| Alendronate Monosodium Trihydrate | 1.3% w/w |
| Citric Acid | 1.0 |
| Sodium Citrate | 0.5 |
| Cellulosic Polymer | 1.0 |
| Corn Starch | 5.0 |
| Sodium Starch Glycolate | 5.0 |
| Titanium Dioxide | 0.5 |
| Vanillin | 0.5 |
| Hydrogenated Castor Oil | 6.0 |
| Povidone | 5.0 |
| Acetylated Monoglycerides | 1.0 |
| Microcrystalline Cellulose | 18.0 |
| Lactose | 55.2 |

The resulting tablets are useful for administration in accordance with the methods of the present invention for inhibiting, i.e. treating or reducing the risk of, dental resorptive lesions in a mammal in need thereof.

Similarly, tablets comprising other relative weights of alendronate, on an alendronic acid active weight basis are prepared.

Also, tablets containing other bisphosphonates at appropriate active levels are similarly prepared: e.g., cimadronate, ibandronate, neridronate, olpandronate, risedronate, piridronate, pamidronate, zoledronate, and pharmaceutically acceptable salts thereof. In addition, tablets containing combinations of bisphosphonates are similarly prepared.

In addition to the ingredients exemplified above, formulations can also contain additional suitable buffers, colors, dispersants, flavors, stabilizers and preservatives as necessary.

DISTRIBUTION OF ALENDRONATE IN FELINE ORAL CAVITY

In a study in which $^{14}C$ labelled alendronate is administered as a single intravenous dose, 0.03 mg/kg, to each of three cats, it is found about 24 hours later that the drug level in the maxilla is about two times the levels found in the long bones, e.g., the tibia and femur. In addition, the accompanying autoradiograph (FIG. 1) shows higher levels of alendronate on the subgingival tooth surface and the surrounding alveolar bone than elsewhere in the maxilla. These data show that the alendronate is preferentially delivered to the site where the lesions most frequently originate. i.e. the jaws, and in particular the subgingival tooth surface and surrounding alveolar bone.

What is claimed is:

1. A method for treating feline dental resorptive lesions in a cat in need thereof comprising administering to said cat a therapeutically effective amount of a bisphosphonate or a pharmaceutically acceptable salt thereof.

2. The method of claim 1 wherein said bisphosphonate corresponds to the chemical structure

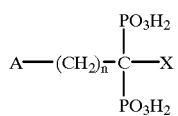

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring; and the pharmaceutically acceptable salts thereof.

3. The method of claim 1 wherein said bisphosphonate is selected from the group consisting of alendronate, cimadronate, clodronate, tiludronate, etidronate, ibandronate, neridronate, olpandronate, risedronate, piridronate, pamidronate, zoledronate, pharmaceutically acceptable salts thereof, and mixtures thereof.

4. The method of claim 3 wherein said bisphosphonate is alendronate, pharmaceutically acceptable salts thereof, and mixtures thereof.

5. The method of claim 4 wherein said pharmaceutically acceptable salt is alendronate monosodium trihydrate.

6. A method of alleviating pain associated with feline dental resorptive lesions in a cat in need thereof comprising administering to said mammal a therapeutically effective amount of a bisphosphonate or a pharmaceutically acceptable salt thereof.

7. The method of claim 6 wherein said bisphosphonate corresponds to the chemical stricture

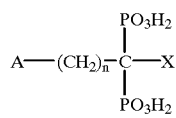

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring; and the pharmaceutically acceptable salts thereof.

8. The method of claim 6 wherein said bisphosphonate is selected from the group consisting of alendronate, cimadronate, clodronate, tiludronate, etidronate, ibandronate, neridronate, olpandronate, risedronate, piridronate, pamidronate, zoledronate, pharmaceutically acceptable salts thereof, and mixtures thereof.

9. The method of claim 8 wherein said bisphosphonate is alendronate, pharmaceutically acceptable salts thereof, and mixtures thereof.

10. The method of claim 9 wherein said pharmaceutically acceptable salt is alendronate monosodium trihydrate.

11. A method for treating or reducing the risk of tooth loss associated with feline dental resorptive lesions in a cat in need thereof comprising administering to said cat a pharmaceutically effective amount of a bisphosphonate or a pharmaceutically acceptable salt thereof.

12. The method of claim 11 wherein said bisphosphonate corresponds to the chemical structure

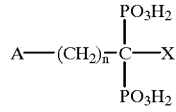

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3–C10 ring; and the pharmaceutically acceptable salts thereof.

13. The method of claim 11 wherein said bisphosphonate is selected from the group consisting of alendronate, cimadronate, clodronate, tiludronate, etidronate, ibandronate, neridronate, olpandronate, risedronate, piridronate, pamidronate, zoledronate, pharmaceutically acceptable salts thereof, and mixtures thereof.

14. The method of claim 13 wherein said bisphosphonate is alendronate, pharmaceutically acceptable salts thereof, and mixtures thereof.

15. The method of claim 14 wherein said pharmaceutically acceptable salt is alendronate monosodium trihydrate.

16. A method for delivering a bisphosphonate or a pharmaceutically acceptable salt thereof to the subgingival tooth surface and alveoli dentales of a cat with feline dental resorptive lesions comprising administering a therapeutically effective amount of said bisphosphonate to a cat in need thereof such that at about 24 hours after administration the resulting average concentration of said bisphosphonate at said subgingival tooth surface and alveoli dentales is at least about two times greater than the average concentration in the diaphysis of the femur.

17. The method of claim 16 wherein said bisphosphonate corresponds to the chemical structure

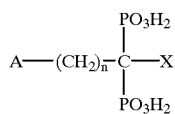

wherein n is an integer from 0 to 7 and wherein A and X are independently selected from the group consisting of H, OH, halogen, $NH_2$, SH, phenyl, C1–C30 alkyl, C3–C30 branched or cycloalkyl, C1–C30 substituted alkyl, C1–C10 alkyl substituted $NH_2$, C3–C10 branched or cycloalkyl substituted $NH_2$, C1–C10 dialkyl substituted $NH_2$, C1–C10 alkoxy, C1–C10 alkyl substituted thio, thiophenyl, halophenylthio, C1–C10 alkyl substituted phenyl, pyridyl, furanyl, pyrrolidinyl, irnidazolyl, imidazopyridinyl, and benzyl, such that both A and X are not selected from H or OH when n is 0; or A and X are taken together with the carbon atom or atoms to which they are attached to form a C3–C10 ring; and the pharmaceutically acceptable salts thereof.

18. The method of claim 16 wherein said bisphosphonate is selected from the group consisting of alendronate, cimadronate, clodronate, tiludronate, etidronate, ibandronate, neridronate, olpandronate, risedronate, piridronate, pamidronate, zoledronate, pharmaceutically acceptable salts thereof, and mixtures thereof.

19. The method of claim 18 wherein said bisphosphonate is alendronate, pharmaceutically acceptable salts thereof, and mixtures thereof.

20. The method of claim 19 wherein said pharmaceutically acceptable salt is alendronate monosodium trihydrate.

* * * * *